United States Patent [19]

Sacherer et al.

[11] Patent Number: 4,717,018
[45] Date of Patent: Jan. 5, 1988

[54] CONTAINER FOR LONGITUDINALLY EXTENDING DIAGNOSTIC TEST STRIPS

[75] Inventors: Klaus D. Sacherer, Kirchheim/Weinstr.; Erich Weiss, Manheim; Jochen Koehn; Ulrich Brach, both of Zell/Mosel, all of Fed. Rep. of Germany

[73] Assignee: Boehringer Mannheim GmbH, Mannheim, Fed. Rep. of Germany

[21] Appl. No.: 890,867

[22] Filed: Jul. 28, 1986

Related U.S. Application Data

[62] Division of Ser. No. 744,116, Jun. 12, 1985, Pat. No. 4,615,462.

[30] Foreign Application Priority Data

Jun. 28, 1984 [DE] Fed. Rep. of Germany ....... 3423851
Dec. 22, 1984 [DE] Fed. Rep. of Germany ....... 3447223
Feb. 16, 1985 [DE] Fed. Rep. of Germany ....... 3505454

[51] Int. Cl.$^4$ ...................... B65D 43/24; B65D 81/26; B65D 85/38
[52] U.S. Cl. .................................... 206/305; 206/204; 206/210; 206/569; 220/335; 220/339
[58] Field of Search ................ 206/204, 210, 1.5, 569, 206/305; 215/235; 220/335, 339; 222/498, 545, 556; 16/227, DIG. 13

[56] References Cited

U.S. PATENT DOCUMENTS

| 3,567,085 | 3/1971 | Flores | 206/204 |
|---|---|---|---|
| 4,158,902 | 6/1979 | Chernack et al. | 220/335 |
| 4,172,540 | 10/1979 | Erichson | 220/335 |
| 4,291,818 | 9/1981 | Nozawa et al. | 222/498 |
| 4,403,712 | 9/1983 | Wiesinger | 220/339 |
| 4,414,705 | 11/1983 | Ostrowsky | 220/339 |
| 4,457,458 | 7/1984 | Heinol | 220/335 |
| 4,503,991 | 3/1985 | Joyce | 215/235 |
| 4,573,600 | 3/1986 | Dubach | 220/339 |
| 4,607,768 | 8/1986 | Taber et al. | 222/556 |

FOREIGN PATENT DOCUMENTS

| 7212373 | 3/1973 | Netherlands | 206/204 |
|---|---|---|---|
| 23376 | of 1899 | United Kingdom | 220/20 |

Primary Examiner—Stephen Marcus
Assistant Examiner—Brenda J. Ehrhardt
Attorney, Agent, or Firm—Kane, Dalsimer, Kane, Sullivan and Kurucz

[57] ABSTRACT

A unitary snap hinge made of plastic with two hinge parts which are connected with each other by means of a main joint. A flexible connecting piece is connected with the hinge parts by means of secondary joints, whereby the secondary joints have a distance from the main joint transverse to the joint axis and that the joints are designed as film joints. The hinge parts have the tendency to snap into the one or other end position from a position of an unsteady balance within their own pivot range. The snap hinge is a separate structural element. The one hinge part supports a locking element for a removal opening, the other hinge part supports at least one adapter piece with arresting elements. Thereby, the snap hinge can be mounted on a container or on the locking piece of the same. A snap hinge or other hinge made of plastic and which is part of a lock may have tearable parts on its foldable hinge part which during the first time closing of the lock are fixedly connected with the lower part thereof and are torn off during the first time opening.

13 Claims, 23 Drawing Figures

CONTAINER FOR LONGITUDINALLY EXTENDING DIAGNOSTIC TEST STRIPS

This is a divisional of co-pending application Ser. No. 744,116 filed on June 12, 1985, now U.S. Pat. No. 4,615,462.

BACKGROUND OF THE INVENTION

The invention relates to a one piece snap hinge made of plastic and a container for longitudinally extending diagnostic test carriers.

Snap hinges are known from DE-PS No. 18 13 187 and DE-OS No. 18 08 875. Snap hinges permit a freely movable hinge part to snap into a locking position or an opening position and to remain in either one of these positions. Common plastic snap hinges include a locking member of generally simple and straightforward design, a flexible hinge portion rotatably coupling a cap to the locking member, the cap having a projecting plug portion aligned with an aperture in the locking member to plug the aperture when in a closed position. A tension or spring member may be included proximate to the hinge to provide a spring force for closing the cap.

The two references noted above show hinges by themselves. This is done to show the function of the hinges. When using the hinges on containers or bottles which are injection molded, the hinges together with the container are injection molded in a single operating step. A problem arises in that molding the snap down portion, the hinge, and the receiving or locking piece as a unit limits injection molding to relatively simply constructed containers or, alternately, it requires highly complex injection molds. In addition, due to limits in molding capability, prior art devices have failed to provide a strong spring action for closing the cap or hinge onto the locking member. Design of prior art cap, hinge and locking members has been limited due to integral construction, failing to achieve the potential widespread application of snap hinges.

In addition, prior art snap hinges generally include protruding hinge members when closed, detrimentally affecting the aesthetic appearance of the closure.

Referring now to another embodiment relating to containers for longitudinally extending diagnostic test carriers, these devices are subjected to strict requirements. The term "test strips" as used herein refers to a well-known example of a test carrier. In particular, the reaction layer of these test carriers is very sensitive with respect to moisture. On the other hand, it should be possible to store the test carriers in the package for a plurality of months or even years without impairing their function. Consequently, the packing must be moisture proof over a long period of time. There also must be the possibility to again close the package in a moisture proof manner after the removal of test carriers. The handling of container functions should be relatively simple, in particular when test carriers are involved which should be used immediately by a layman, for example, for self-determination of blood sugar.

In order to meet these requirements, in the past, containers were used wherein the container body consisted of aluminum or glass. They have a circular cross section and they are closed by a circular plug. The moisture tightness is obtained by a flat seal made of rubber in cooperation with a screw locking. More modern embodiments have a plug which is inserted having a sealing face made of plastic adapted to the sealing edge of the removal opening.

These known packages for strip-like test carriers meet the aforementioned technical prerequisites, but the handling of the same leaves much to be desired. For example, diabetics who want to determine the blood sugar level themselves at a regular interval, would like to have a package which could be easier to take along, for example, in the pocket of a jacket, and which permits an easier removal of the test strip.

For other, less demanded products, easy portable flat packages are known which also have easy-to-handle locks. The concept of transferring such structural principals to the packages of test strips has not been followed up, because it was thought it would be useless to fulfill the requirements for test strip packages in this manner. Thus, an essential feature is that the test strip package must be made cost effective, despite its high quality, and must be filled with a high number of test strips.

SUMMARY OF THE INVENTION

Referring now to the snap hinge embodiment, the subject invention provides a hinge (or cap portion) permitting the manufacturing of complicated shaped containers such as, for example, the aforementioned test strip container in the injection molding process, without complicated molds. There is a need to make containers with associated snap hinges in the injection molding process which heretofore could not be made due to their complexity, or could only be made with a high technical apparatus cost. This object is now met in accordance with the present invention.

In accordance therewith, the snap hinge of the present invention is made as a separate structural part allowing simple molds to be used in production, and one of the hinge parts is provided with plug in parts for mounting on the container or on a locking piece of the container.

When constructing the injection molds for the container itself, or its locking piece, one does not have to consider the design of the snap hinge any longer. Moreover, different structural parts are made separately. These parts include the snap hinge, the container (commonly a bottle) and, if desired, a locking piece to be mounted on the container.

One particular favorable structural shape provided by the present invention occurs if the curve-like or angle-like connecting piece is so arranged on the snap hinge that it points toward the container in its locked position, it does not protrude outwardly in any interfering manner when the container is in its locked position. The outer face of the snap hinge is in its locked position a plane (or an arched face adapted to the shape of the container), for example, which contains the main joint, so that a satisfactory aesthetic appearance is provided. No hinge portion protrudes to the outside in an interfering manner.

The increased versatility provided by the present invention of separate molding has been found to permit manufacture of hinges having a broad range of qualities and applications. Stronger spring action may be provided to close the container. Stronger closures are also produced. Freedom of design is provided. In addition, freedom to design body parts to the container is provided.

The joints of the present device can be particularly favorably arranged if the two hinge parts are shaped like a plate and if the plates have a sufficient thickness.

When thin plates are used the secondary joint may attach to protruding bars of the hinge joint. In addition, one hinge part may be provided with one or a plurality of plug pins on the outer shoulder which serve for plugging into corresponding openings on the container or a locking piece.

It is also contemplated that the one hinge part may have only one adapter plug which is provided with an inner shoulder and which serves for being plugged into a corresponding pin in the container or its locking piece. The adapter plug may be so designed that during a plugged in snap hinge it encompasses the orifice of the container, while the other hinge portion is so arranged that it snaps into this socket during closing the orifice.

In furtherance, the invention relates to an originality safety means which is generally usable for hinge locks made of plastic, but specifically for snap hinge locks. Such locks are used for bottles or cans, for example, as they are used in households for cleaning materials or foodstuff, like oil, or for cosmetical goods in liquid or paste-like shape.

The locks have a lower part connected with a container and a lid which are connected with each other by means of a hinge. If a flexible spring is additionally provided, the locks can be so designed that the lid from an unstable balance snaps into either the locking position or the opening position. Locks of the latter mentioned types are known from ES-GM No. 212,300-NOVA- and the DE-OS No. 31 50 493-Wiesinger-.

In accordance with the Spanish petty patent a pull off ring is provided for the originality safety which encompasses the lower part of the lock and is mounted thereon with tear off bridges. Before opening the lock it is torn off, so as to indicate that the lock had been opened. Such originality safety locks fulfill their purpose, but are not aesthetically appealing because of the necessary dimensions of the tear off ring. In addition, the originality safety can be easily circumvented, in that the lock can be opened and again closed with some skill without removing the tear off ring, so that this performance is later not recognizable.

In a further embodiment of the invention an originality safety for snap locks is provided which is made from plastic indicating, on one hand, that the lock already had been opened and, on the other hand, not impairing the aesthetic appearance of the lock without resulting in any substantial increase in the manufacturing costs and costs for mounting a lock onto a container.

Locks in accordance with the two latter mentioned references are made in their open position by means of injection molding. Care must be taken that the parts of the originality safety can be made in the same injection process. Furthermore, care must be taken that, when mounting (in particular during impact) of the lock onto a container, the originality safety is brought into its locking position, without any further operating steps which would render the mounting too expensive.

This object of the invention is solved as follows. During the first mounting of the hinge, or during a first closing of a foldable part, the tearable part may engage into an adaptable counter piece, for example, a recess on the lower part of the lock. Instead, the tearable part itself may be welded to the lower part of the lock. Alternately, plug pins which are available on the tearable part may be welded on the lower part.

The lid of the lock may be provided with lateral extensions which in turn are anchored in the lower part during a first time mounting or closing of the lock in such a manner that they remain securely anchored even during opening. The extensions may be connected with the lid along a perforated line (safety breaking line) or by means of a row of tear off ribs, so that they tear off during the first time opening, but remain in the lower part of the lock, thus indicating that an opening occurred.

In accordance with the present invention the locking piece is optional. The snap hinge may be directly assembled on the container without the interference of a locking member. The locking member merely adapts a conventional container neck for use with a snap hinge. A container neck adapted to directly receive a snap hinge may be used in combination with the snap hinge of the present invention to achieve the objects and advantages discussed herein.

The object of the test carrier container embodiment, of providing a quality storage container with large capacity having structural characteristics of portable flat packages, is achieved by a container in accordance with the present invention. The flattened cross sectional shape permits an easy storing of the container. By mounting the locking element by means of a hinge on the removal end of the container the locking means can no longer be lost. The small cross section of the removal opening facilitates the sealing of the lock because the length to be sealed has been reduced. Moreover, individual test strips can be easily removed by merely turning the package. The removable bottom element permits a rapid filling of the package. In view of the fact that the drying substance is mounted in the container body, instead of the locking means as was heretofore customary, the drying substance is no longer completely subjected to room moisture and consequently its capacity is less quickly exhausted. Preferably, it is mounted in the bottom element. This mounting facilitates the manufacturing of the package.

The container body and the bottom element are preferably made from polyethylene or propylene with a wall thickness of at least about 1.0 mm, so as to obtain a particularly good moisture tightness and mechanical stability of the container. Advantageously, the container body and the bottom element may be connected with each other by means of ultrasound welding. For this purpose, they should be made from the same material.

A further preferred embodiment provides that the hinge is a film hinge which is connected with a snap mechanism as known from U.S. Pat. No. 3,720,979, for example. Such a snap hinge, which is made completely from plastic in the injection molding process, can be made particularly easy in combination with the inventive container if it is produced separately from the same and is then mounted thereon with a suitable clamping or engagement means such as described above with respect to the subject hinge invention.

Exemplified examples with further features of the invention are described in conjunction with the drawings.

Figure 15:
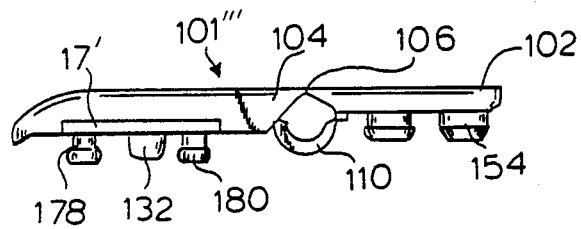
FIGS. 15 and 16 are a side view and a plan view of a fourth embodiment of a snap hinge similar to the one of FIGS. 6 and 7 having lateral extensions for an originality safety.
Figure 16:
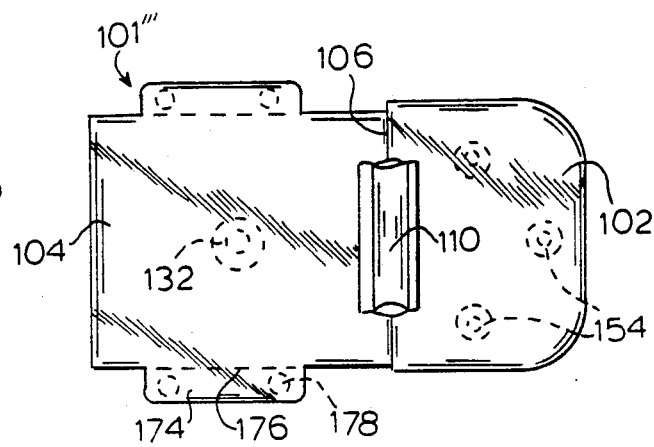
Figure 17:
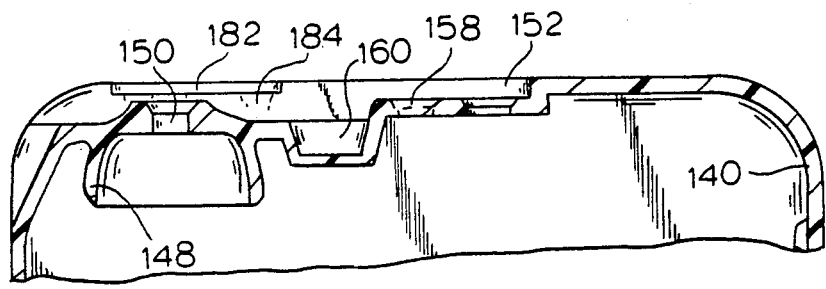
Figure 18:
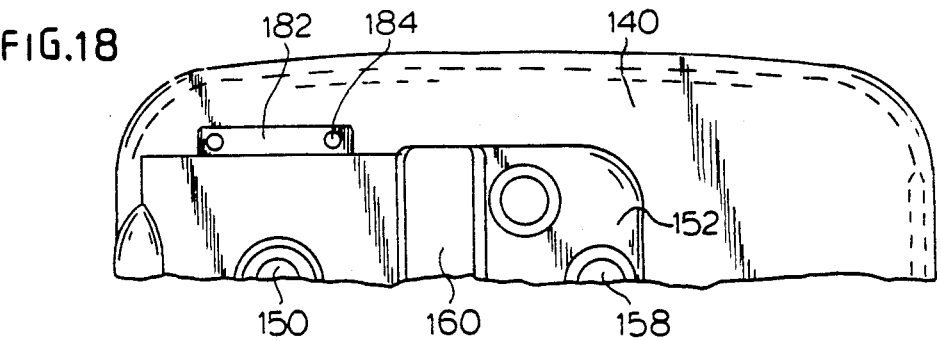

FIGS. 17 and 18 each show, in a central longitudinal sectional view and plan view, one part of a locking piece for receiving a snap hinge in accordance with FIGS. 15 and 16.

Figure 19:
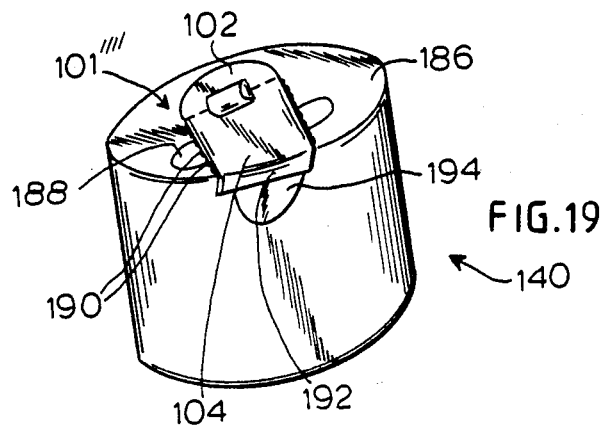

FIG. 19 perspectively illustrates a fifth embodiment of a locking piece with a lid and inserted snap hinge with originality safety.

Figure 20:
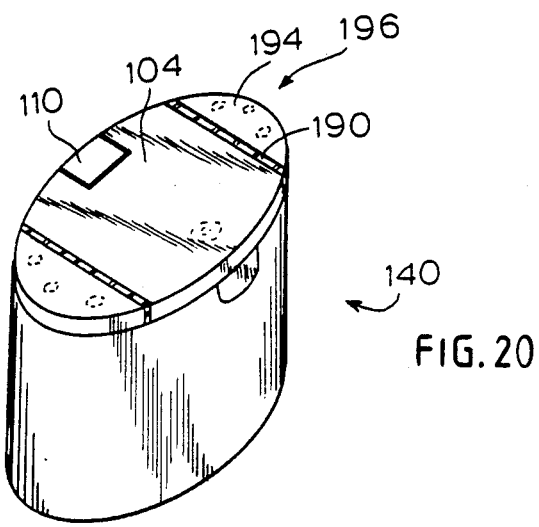

FIG. 20 perspectively shows a sixth embodiment.

Figure 21:
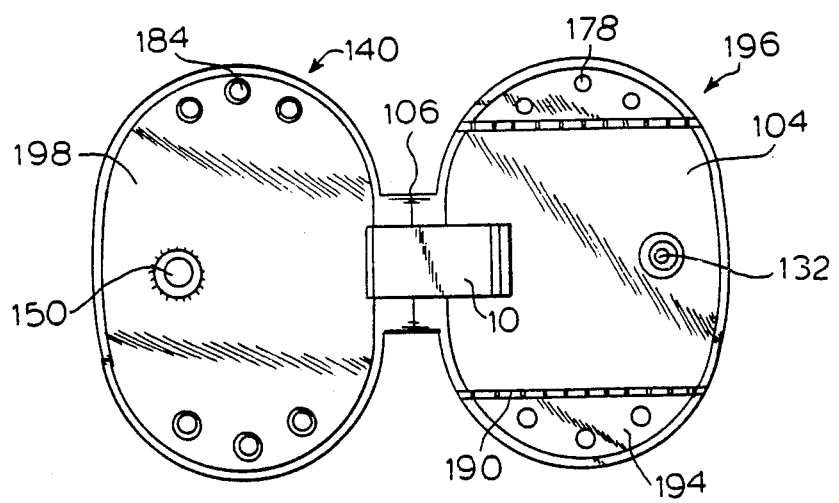

FIG. 21 shows the lower part and the lid of the sixth embodiment opened in a plan view.

Figure 22:
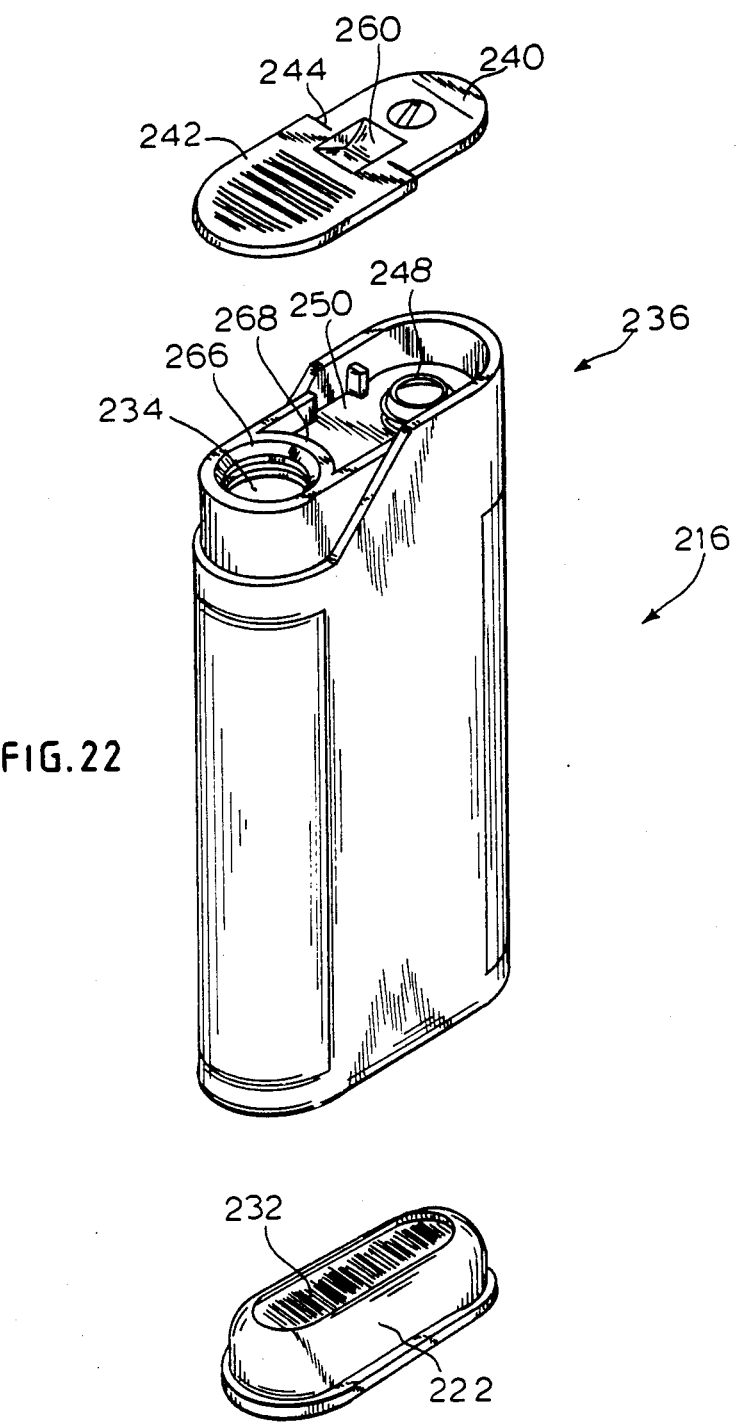

FIG. 22 is a perspective illustration of an inventive container with removed bottom element and locking element.

Figure 23:
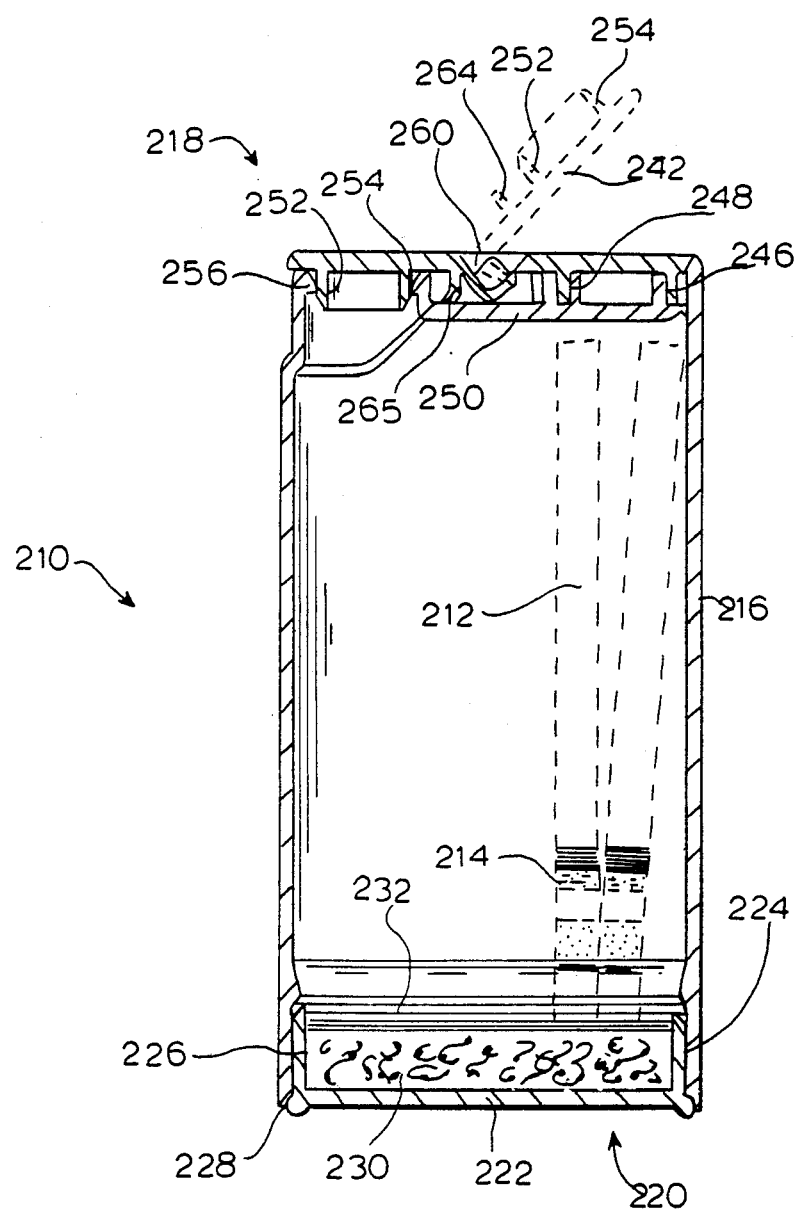

FIG. 23 is a cross section through an inventive container in the assembled condition.

The terms "above", "below" and the like in all exemplified embodiments always relate to the position of a snap hinge on an upright standing container, whereby the orifice is directed upwardly.

All illustrated snap hinges are injection molded in one piece, for example, from polypropylene.

FIRST EMBODIMENT

The snap hinge 1 illustrated in FIGS. 1 to 3 and 5 has two plate like hinge parts 2 and 4 which are connected with each other by a main joint 6 in form of a film hinge. The main joint is designed in two parts. An opening 8 is provided between its two parts in which a flexible connecting piece 10 is mounted. The connecting piece 10 is connected with the hinge parts 2 and 4 by means of two secondary joints 12 and 14. An adapter plug 16 is provided on the hinge part 2 which is provided with an inner shoulder 18.

Figure 1:
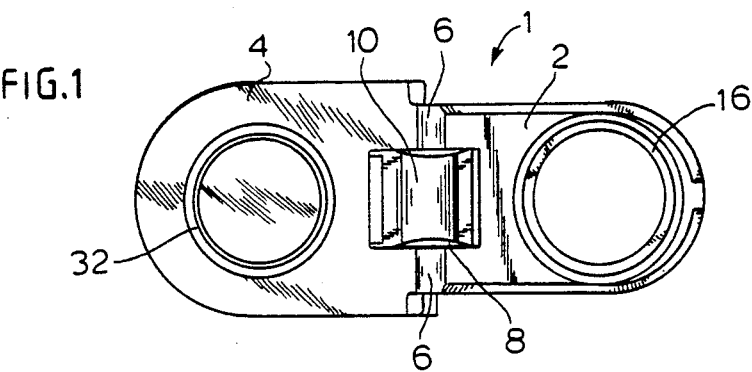
FIG. 1 is a view from below of a first embodiment of a snap hinge in accordance with the invention.
Figure 2:
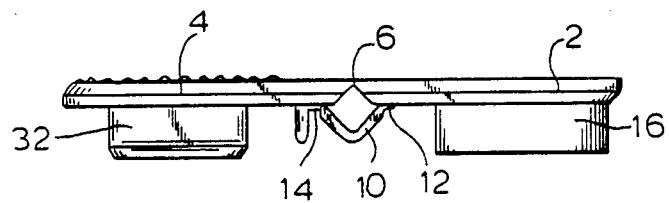
FIG. 2 is a side view of the same snap hinge.
Figure 3:
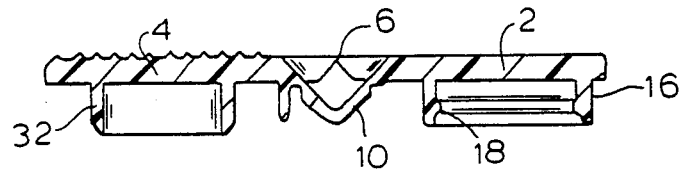
FIG. 3 is a central longitudinal sectional view through this snap hinge.
Figure 4:
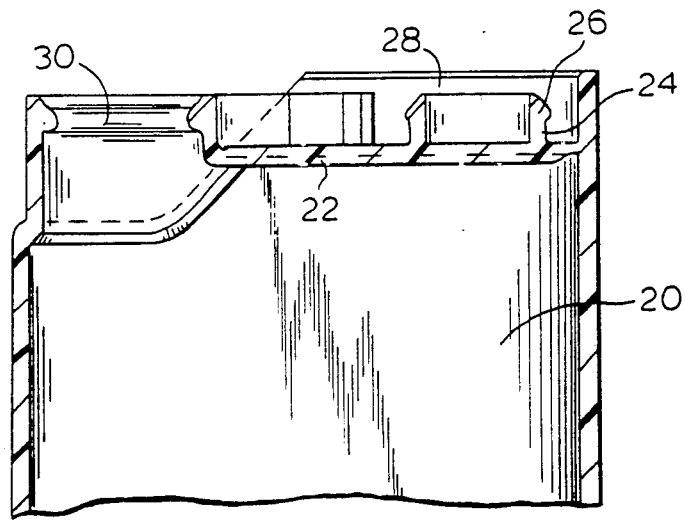
FIG. 4 is a central longitudinal view through the upper part of a container to be closed by a snap hinge.

An adapter plug 24 which functions as a plug pin and which has an outer shoulder is mounted on a container 20 (FIG. 4), of which only the upper end is shown, that is, on an upper end plate 22. The hinge part 2 can be anchored on the adapter plug 24 of the container with the assistance of its adapter plug 15. A wall 28 of the container which extends around the end plate 22 permits a uniform orientation of snap hinge 1.

At the left side the container has a removal opening 30. An adaptable locking element 32 in form of a socket is provided on the hinge part 4. Moreover, a plate like part 34 in the width of the flexible connecting piece 10 is provided on hinge part 4.

Structural parts of the same or similar function in the Figs. of the following embodiments are designated with the same reference numerals as in the first embodiment.

SECOND EMBODIMENT

Figure 6:
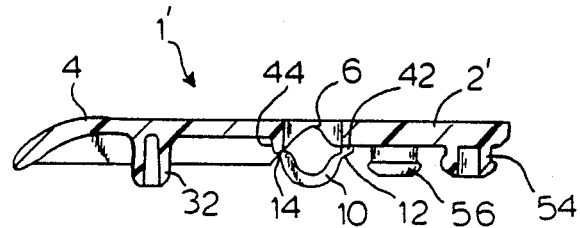
FIG. 6 illustrates a snap hinge in accordance with a second embodiment of the invention shown in a central longitudinal section.
Figure 7:
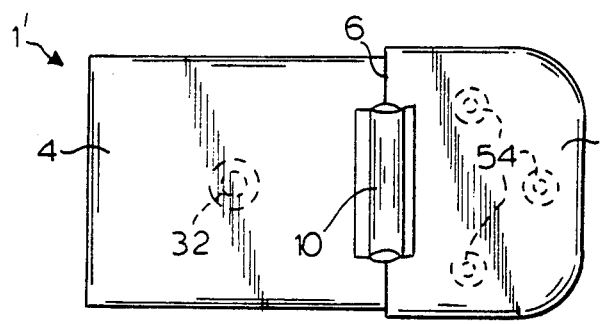
FIG. 7 illustrates the snap hinge of FIG. 6 in a plan view from outside (above).
Figure 14:
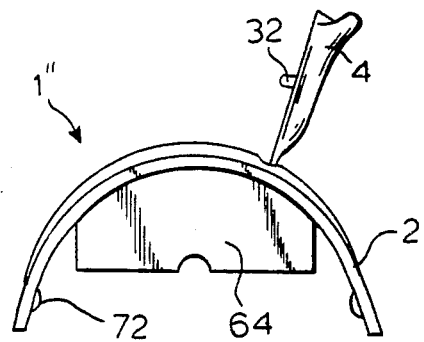
FIG. 14 (page 2) is a side view in accordance with Fig. 10 of the snap hinge in an open position.
Figure 8:
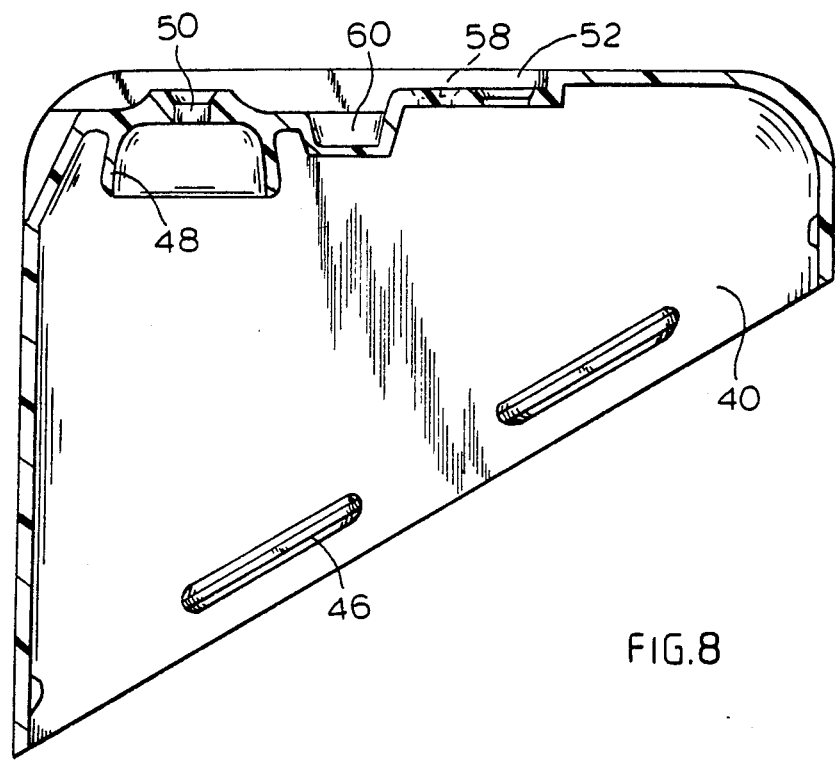
FIG. 8 is a central longitudinal sectional view illustrating a locking piece of a snap hinge in accordance with FIGS. 6 and 7 for mounting on a container.
Figure 9:
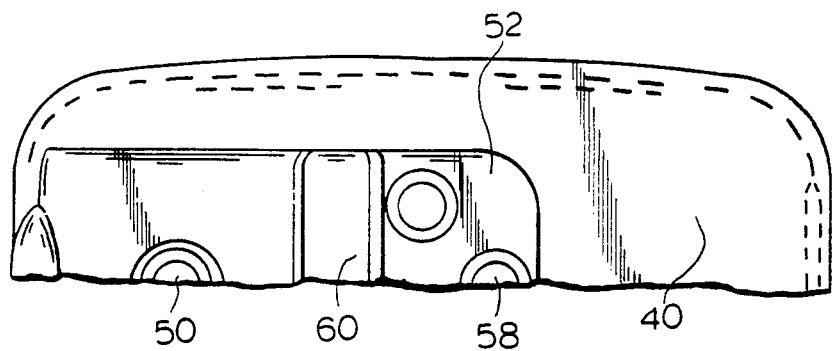
FIG. 9 is a plan view of a part of the locking piece of FIG. 8 from above.
Figure 10:
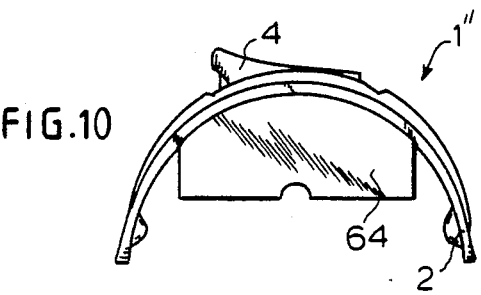
FIG. 10 illustrates a third embodiment of a snap hinge in accordance with the invention in a side view.
Figure 11:
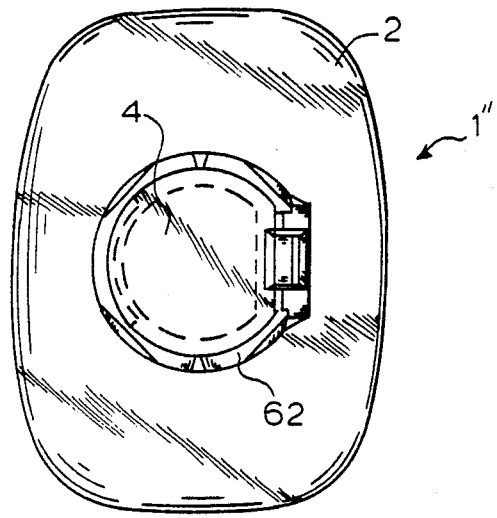
FIG. 11 is a plan view of the snap hinge of FIG. 10.
Figure 12:
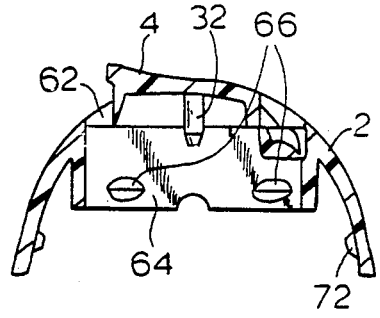
FIG. 12 is a central vertical cross sectional view through the snap hinge of FIG. 10.
Figure 13:
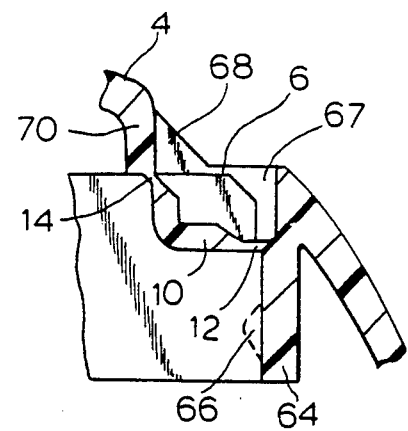
FIG. 13 is a detail of the snap hinge of FIG. 10, illustrating the joints.

FIGS. 6 and 7 illustrate a snap hinge 1' which is to be attached not directly on a container but on a locking piece in accordance with FIGS. 8 and 9, which in turn has to be mounted on a container. While the flexible connecting piece 10 is wound in the first embodiment, it is designed curve like in this embodiment. However, it has the same function. In accordance with FIG. 6 the two secondary joints 12 and 13 do not seat directly on the hinge parts 2 and 4, but are mounted on bars 42 and 44 which protrude from the hinge parts 2 and 4 downwardly.

The locking piece 40 illustrated in FIGS. 8 and 9 is designed as a cap with an oblique lower edge. In the proximity of its lower edge the cap is provided with snap shoulders 46 which engage into corresponding recesses of a container (not shown) after being plugged in. The upper left inner side the locking piece is provided with a cup 48 which should surround the container orifice. Centrically thereto a discharge opening 50 is provided. An adaptable locking element 32 in form of a hollow pin is provided on the snap hinge 1'.

The upper side the locking piece has a flat recess 52 for receiving the snap hinge. Three plug pins 54 are provided on the hinge part 2 which each have an outer annular shoulder 56 at their lower end. The plug pins can be impressed into continuous openings 58 of locking piece 40 and are secured against sliding out by means of their annular shoulders 56 and retain the hinge part 2 in the flat recess 52 of the locking pieces.

A recess in the form of a transverse extending trough 60 is provided in the cover plate of the locking piece for accommodating the flexible connecting piece 10.

Figure 5:
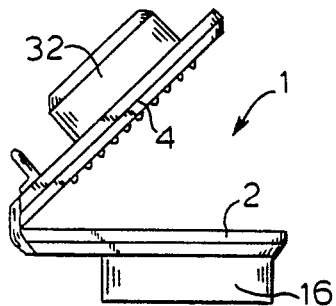
FIG. 5 illustrates a side view of the snap hinge of FIG. 2, the hinge being opened.

The open position of the snap hinge looks similar to the one of FIG. 5.

THIRD EMBODIMENT

The snap hinge 1'' illustrated in FIGS. 10 to 14 (second page of FIG. 14) again has a hinge part 4 with a locking element 32 in the form of a pin for an orifice of a bottle. In contrast to the two preceding embodiments the hinge part 4 is mounted within an opening 62 of the hinge parts 2. The hinge part 2 as a whole serves as a plug part and has support cams 72. Moreover, an adapter plug 64 is molded therein which has inner located cams 66 and serve for mounting on the orifice of a bottle. The main joint 6 is located between the protrusions 67 (which extend slightly inwardly from the adapter plug) and protrusions 68 of the hinge joints 4. The flexible connecting piece 10 supports with its secondary joint 14 on the inner wall of the adapter plug 64 and with its secondary joint 14 on a straight short sidewall 70 of the hinge part 4.

FOURTH EMBODIMENT

The FIGS. 15 and 16 illustrate a snap hinge 101'', as had been described in conjunction with FIGS. 6 and 7. It is provided with two lateral extensions 174. The extensions are made unitary with the hinge part 104 by means of injection molding. On each a safety breaking line 176 is provided between the extensions and the hinge part 104 in the form of a perforation. Therefore, the extensions can tear off at this place. Each extension has two downwardly extending plug pins 178 with one each annular shoulder 180.

The associated locking piece 140 is provided with lateral flat indentations 182 adaptable for the extensions 174 of hinge part 104 at both sides of its recess 152 for receiving the snap hinge 101". The holes 184 are provided for receiving the plug pins 178 which extend from the bottom of the indentations through the wall of the locking piece 140.

The snap hinge 101" and the locking piece 140 are injection molded in one unitary piece in the same manner as in the second embodiment. When compressing (impacting) the snap hinge on the locking piece, not only is the hinge part 102 anchored in the locking piece with the assistance of plug pins 154, but also the extensions 174 in the indentations 182 and the holes 184 with the assistance of their plug pins 178. Thus, the hinge part 104 is secured on locking piece 140. During the first time opening the extensions 174 tear off from hinge part 104 along the safety breaking lines 176. This hinge part is normally used as a closing lid. The extensions 174 remain at their places and indicate that the lock had been opened.

FIFTH EMBODIMENT

A snap hinge 101"" is provided on a locking piece 140 in the embodiment in accordance with FIG. 19 which has an oval cross section. The upper wall 186 of the locking piece is again provided with a recess in which a snap hinge 101"" is mounted. The hinge part 102 is welded into wall 186. The hinge part 104 is a unitary piece with two tear off lugs which are connected with the hinge parts by means of tear off ribs 190. The tear off lugs 188 are welded into flat indentations of the upper wall 186.

The hinge parts 102, 104 and the tear off lugs 188 with their associated tear off ribs are injection molded as a unitary piece. The hinge part 104 has a downwardly deflected segment 192. By means of a locking recess 194 in the jacket of the locking piece 140"", the lower edge of segment 192 can be well locked.

The tear off ribs 190 break during the first time upwardly folding of hinge part 140, while the tear off lugs 188 remain at their place. The broken tear off ribs indicate the opening.

SIXTH EMBODIMENT

While in the fourth and fifth embodiment a snap hinge is used as a separate structural element which is inserted into a locking piece, the snap hinge and the locking piece are injection molded as a unitary piece in the sixth embodiment, that is, in the opening position of the snap hinge in accordance with FIG. 21. The foldable hinge part 140 is connected with side parts 194 by means of tear off ribs 190. The locking part 104 and the side parts together form a lid 196 for the lower part 140 which is closed by a cover plate 198. In a known manner, the cover plate is provided with a discharge opening 150 which is closeable by means of a locking element 132, for example, a mandrel. The lid is pivotable around main joints 106. A flexible connecting piece 110 provides the required snap performance during opening and closing.

The side parts 194 of the lid are provided with plug pins 178 and corresponding holes 184 are mounted in cover plate 198.

During the first time locking of the lid 194, the plug pins 178 are pressed into holes 184 and anchor the side parts 194 securely on the lower part of the locking piece 140. During the first time opening of the hinge part 104, the tear off ribs 190 tear off and indicate the opening.

MODIFICATIONS OF THE FOURTH TO THE SIXTH EMBODIMENT

For an improved security the plug pins 178 (as well as 154) may be welded with the lower part of the cover plate which is apertured with the holes, after the impressing into the holes 184. Instead, the extensions 174 and the side parts 194 without the plug pins may be face welded or spot welded with the lower cover plate.

SEVENTH EMBODIMENT

The container 210 of FIG. 22 contains a plurality of test strips, for example, 25 or 50 pieces. Only two test strips 212 are indicated by dashed lines, so as to make clear their positions in the inner chamber of container 210. One also recognizes the reaction fields 214 on the test strips 212.

The container consists of a container body 216 and a locking means which in its totality is designated with the reference number 218.

The container bottom 220 of the container 210 is formed by a bottom element 222 which is inserted into the container body 216. For this purpose the container body has a recess 224 in which a cylindrical protrusion 226 of the bottom element 222 is inserted. The protrusion 226 is snugly adapted to the recess 224. At the outermost edge of the bottom element it is connected with the recess 224 by means of ultrasound welding.

A chamber 230 with a drying substance is provided within bottom element 222. The chamber is closed toward the inner chamber of the container 210 with an element which regulates the moisture absorption, for example, a carton disc 232.

As can be clearly seen from FIG. 22, the container 210 has a substantively flattened oval cross section in the illustrated exemplified embodiment. An elliptical cross section would also be suitable, however the oval shape is the preferred one. FIG. 22 clearly shows the removal opening 34 which is approximately concentric with the one semicircle of the oval. This arrangement facilitates the removal of test strips, because the package must only be tilted in the direction of the removal opening.

The removal opening marks the removal end 236 of the container body 216. The locking parts 238 are mounted thereon. It essentially consists of a mounting shank 240 and a locking shank 242 which are connected with each other by means of a film hinge 244.

The mounting shank 240 has a circular shaped protrusion 246 which transgresses a corresponding circular shaped protrusion 248 which is mounted on the substantially oval end face 250 which closes the container body 216 upwardly. The end face 250 is an integral part of container body 216. Therefore, the only upward opening of the container body 16 is the preferred circular removal opening 234. This is closed by a locking element 252 which is mounted on the locking shank 242 of the locking part 238. It can be seen that in the subject case the locking element 252 is formed by a circular shaped protrusion extending vertically from the locking shank 242. The outer face of this protrusion forms the sealing face 254 which sealingly engages on a sealing edge 256 of the removal opening in the closed condition illustrated in FIG. 23. In the illustrated preferred embodiment the sealing edge of the container is conically shaped toward the inside of the container. The structure has a relatively thick wall, so that the sealing edge 256 does not yield much when closing the container. In contrast thereto, the locking element 252 is relatively thin walled and is slightly compressed in the direction of the center of the opening during closing. Here, a round removal opening 234 is shown to be favorable, because the also circular locking element 252 has a favorable circular characteristics.

FIG. 23 predominantly illustrates the closed position of the locking shank. Moreover, the open position thereof is recognizable by the dash line illustration. The connection between the locking shank 242 and the mounting shank 240 is shaped in known manner by a film hinge and a snap spring 260 made from the same material. The snap spring 260 is also connected with the two shanks 240 and 242 by means of shanks, whereby the axis of these film hinges are different from the one of film hinge 244 and are provided in such a manner that a snap effect is obtained. When moving the locking shank 242 from the open position illustrated in dashed lines FIG. 23 into the closed position illustrated in full lines, a dead point is overcome. From this dead point the snap spring 260 executes a movement of the locking shank 242 into the open as well as closed position.

More details concerning the function of this snap mechanism can be seen from already cited U.S. Pat. No. 3,720,979. A particularity of the structure selected here consists in that the snap spring 260 does not arch out of the package but arches inwardly into the direction of the inside of the package.

A substantial safety function is obtained by the protrusion 264 which extends about vertically from the locking shank 242. It is so arranged and dimensioned that its tip 265 abuts on the outer side of shoulder 266 of the removal opening 234. If no additional pressure is exerted on the locking shank 242 in the closing direction at this point of the pivot path of the locking shank 242, it remains in one position which clearly indicates that the package has not yet been closed properly. By means of an additional light pressure the protrusion 64 can be moved past the abutment 268 of shoulder 266 so as to completely close the package. This measure permits visual verification that, when put aside, the package is completely closed.

What is claimed is:

1. Container (210) for longitudinally extending diagnostic test carriers (212) comprising:
   a longitudinally extending container body (216) for receiving the test carrier (212), whose inner space length is larger than the length of the test carrier (212) with a removal end (236) at which the removal opening (234) is disposed and with a container bottom (220) at the end facing away from the removal end (236) of the container body (216), and
   a locking means (218) for locking the container body (216) in a moisture proof manner, wherein
   the container body (216) and the locking means (218) are injection molded parts,
   the container body (216) has a flattened cross section in a plane transverse to its longitudinal direction deviating from the circular shape,
   a locking element (252) having a protrusion is mounted on a locking shank (242) which is pivotably mounted at the removal end (236) of said container body (216) by means of a hinge (244),
   the locking shank carries the protruding locking element (252) having a sealing face (254) adapted to seal with a sealing edge (256) of the removal opening (234),
   the cross section of said removal opening (234) is considerably smaller than the cross section of the container body (216),
   the container bottom (220) encompasses a bottom element (222) being separate from the remainder of the container body (216) and moisture proof connected therewith, and
   the container body (216) encompasses a chamber for receiving a drying substance.

2. Container in accordance with claim 1, characterized in that said bottom element (222) encompasses a chamber (230) with a drying substance which is closed toward the inside of said container with an element (232) which regulates the moisture supply.

3. Container in accordance with claim 2, characterized in that said container body (216) including said bottom element (222) consists of polyethylene or polyethylene or polypropylene having a wall thickness of at least 1 mm.

4. Container in accordance with claim 3, characterized in that said locking element (252) with its associated sealing face (254) is designed as a circular protrusion protruding vertically from said locking shank (242) being elastically compressible toward its center, whereby said sealing face (254) has a circular cross section.

5. Container in accordance with claim 4, characterized in that said locking shank (242) is a separate part from container body (216) and is connected therewith by means of a clamping and/or locking connection (246,248) which encompasses said locking shank (242), a mounting shank (240), and a plastic film hinge (244) with a snap spring (260) connecting said two shanks.

6. Container in accordance with claim 5, characterized in that said locking shank (242) is provided with a protrusion (246) being so disposed that it engagingly abuts against an associated abutment (268) of said container body (216) during the closing of the container, so that a noticeable resistance must be overcome for the continuation of the closing movement.

7. Container in accordance with claim 1, characterized in that said locking means (218) comprises a snap hinge wherein the snap hinge is separate from the container body.

8. Container in accordance with claim 7, wherein the snap hinge comprises two hingedly connected parts, said parts being the locking shank (242) and a mounting shank (240).

9. Container in accordance with claim 8, further comprising a film hinge hingedly connecting the locking shank and the mounting shank.

10. Container in accordance with claim 9, wherein the mounting shank (240) has a first protrusion (246) which couples to a corresponding second protrusion (248) mounted on the container body to secure the mounting shank (240) to the container body.

11. Container in accordance with claim 10, wherein the locking shank comprises a locking element (252) mounted thereon, the outer portion of which forms a sealing face (254) which sealingly engages on a sealing edge (256) of the removal opening (234) in the container body.

12. Container in accordance with claim 8, further comprising a safety protrusion (264) mounted on the locking shank (242), so dimensioned that its tip (265) abuts on an outer side of shoulder (266) of the removal opening (234) thereby requiring additional pressure to move the locking shank past a first position to seal the container body wherein in the first position a clear indication is provided that the package has not yet been closed properly.

13. Container in accordance with claim 9, further comprising a snap spring (260) located between the mounting shank and the locking shank and composed of plastic, the snap spring having a first and second spring part affixed by a spring film hinge therebetween wherein the axis of the spring film hinge and film hinge (244) are spatially offset in such a manner that a snap effect is obtained.

* * * * *